US012733935B2

(12) United States Patent
Pancholy

(10) Patent No.: US 12,733,935 B2
(45) **Date of Patent: *Sep. 15, 2026**

(54) METHOD TO STOP BLEEDING, WITH SHORT HEMOSTASIS DURATION USING A LOW DOSE OF ANTICOAGULANT

(71) Applicant: Samir Bipin Pancholy, Clarks Summit, PA (US)

(72) Inventor: Samir Bipin Pancholy, Clarks Summit, PA (US)

(73) Assignee: Vasoinnovations Inc., South Pasadena, CA (US)

( * ) Notice: Subject to any disclaimer, the term of this patent is extended or adjusted under 35 U.S.C. 154(b) by 121 days.

This patent is subject to a terminal disclaimer.

(21) Appl. No.: 18/951,638

(22) Filed: Nov. 18, 2024

(65) Prior Publication Data

US 2025/0072898 A1 Mar. 6, 2025

Related U.S. Application Data

(63) Continuation of application No. 17/736,213, filed on May 4, 2022, now Pat. No. 12,178,436, which is a continuation of application No. 16/829,317, filed on Mar. 25, 2020, now Pat. No. 11,350,943, which is a continuation of application No. 15/924,273, filed on Mar. 18, 2018, now Pat. No. 10,639,042, which is a continuation of application No. 15/426,056, filed on Feb. 7, 2017, now Pat. No. 9,949,738, which is a continuation-in-part of application No. 15/340,023, (Continued)

(51) Int. Cl.
*A61B 17/12* (2006.01)
*A61B 17/132* (2006.01)
*A61B 17/135* (2006.01)

(52) U.S. Cl.
CPC ........ *A61B 17/12* (2013.01); *A61B 17/12009* (2013.01); *A61B 17/1325* (2013.01); *A61B 17/135* (2013.01); *A61B 2017/12004* (2013.01)

(58) Field of Classification Search
CPC .............. A61B 17/12; A61B 17/12009; A61B 17/1285; A61B 17/132; A61B 17/1322; A61B 17/1325; A61B 17/135; A61B 2017/00829; A61B 2017/00902; A61B 2017/12004

See application file for complete search history.

(56) References Cited

U.S. PATENT DOCUMENTS 9,308,000 B2 * 4/2016 Pancholy ............ A61B 17/135
9,510,838 B2 * 12/2016 Pancholy ............ A61B 17/135

(Continued)

*Primary Examiner* — Ryan J. Severson
(74) *Attorney, Agent, or Firm* — Rajendra Gurudas Sardesai

(57) ABSTRACT

Disclosed are methods and devices for obtaining patent hemostasis of the radial artery by compressing the uninstrumented ulnar artery to increase radial artery flow. The device comprises a band having an inflatable bladder for applying blunt pressure to the ulnar artery. The method comprises applying a pressure to the homolateral ulnar artery and applying a pressure to the radial artery at the access site to obtain hemostasis at the access site. The method further comprises administering an anticoagulant to a patient at a dose ranging from about 20 units per kg of body weight to about 30 units per kg of body weight.

20 Claims, 4 Drawing Sheets

Related U.S. Application Data filed on Nov. 1, 2016, now Pat. No. 9,592,060, which is a continuation of application No. 15/062,150, filed on Mar. 6, 2016, now Pat. No. 9,510,838, which is a continuation of application No. 13/941,219, filed on Jul. 12, 2013, now Pat. No. 9,308,000.

(60) Provisional application No. 62/405,951, filed on Oct. 9, 2016.

(56) References Cited

U.S. PATENT DOCUMENTS

| | | | | |
|---|---|---|---|---|
| 9,592,060 | B2 * | 3/2017 | Pancholy | A61B 17/135 |
| 9,949,738 | B2 * | 4/2018 | Pancholy | A61B 17/12009 |
| 10,213,212 | B2 * | 2/2019 | Pancholy | A61B 17/135 |
| 10,213,214 | B2 * | 2/2019 | Pancholy | A61B 17/12 |
| 10,245,041 | B2 * | 4/2019 | Pancholy | A61B 17/12009 |
| 10,342,545 | B2 * | 7/2019 | Pancholy | A61B 17/12 |
| 10,342,551 | B2 * | 7/2019 | Pancholy | A61B 17/12 |
| 10,639,042 | B2 * | 5/2020 | Pancholy | A61B 17/12 |
| 10,716,576 | B2 * | 7/2020 | Pancholy | A61B 17/135 |
| 10,722,245 | B2 * | 7/2020 | Pancholy | A61B 17/12 |
| 10,722,246 | B2 * | 7/2020 | Pancholy | A61B 17/12009 |
| 10,987,109 | B2 * | 4/2021 | Pancholy | A61B 17/135 |
| 11,350,943 | B2 * | 6/2022 | Pancholy | A61B 17/12009 |
| 11,653,932 | B2 * | 5/2023 | Pancholy | A61B 17/1325 606/202 |
| 12,178,436 | B2 * | 12/2024 | Pancholy | A61B 17/12009 |
| 2015/0018868 | A1 * | 1/2015 | Pancholy | A61B 17/1325 606/202 |
| 2016/0183951 | A1 * | 6/2016 | Pancholy | A61B 17/135 606/202 |
| 2017/0042552 | A1 * | 2/2017 | Pancholy | A61B 17/135 |
| 2017/0135702 | A1 * | 5/2017 | Pancholy | A61B 17/1325 |
| 2017/0143346 | A1 * | 5/2017 | Pancholy | A61B 17/135 |
| 2018/0000495 | A1 * | 1/2018 | Pancholy | A61K 31/727 |
| 2018/0206847 | A1 * | 7/2018 | Pancholy | A61B 17/12 |
| 2019/0015106 | A1 * | 1/2019 | Pancholy | A61B 17/12009 |
| 2019/0015111 | A1 * | 1/2019 | Pancholy | A61B 17/12009 |
| 2019/0021743 | A1 * | 1/2019 | Pancholy | A61B 17/12 |
| 2019/0150939 | A1 * | 5/2019 | Pancholy | A61B 17/135 |
| 2019/0150940 | A1 * | 5/2019 | Pancholy | A61B 17/1325 |
| 2019/0150941 | A1 * | 5/2019 | Pancholy | A61B 17/135 |
| 2019/0175192 | A1 * | 6/2019 | Pancholy | A61B 17/1325 |
| 2020/0222052 | A1 * | 7/2020 | Pancholy | A61B 17/135 |
| 2020/0289130 | A1 * | 9/2020 | Pancholy | A61B 17/12 |
| 2020/0315631 | A1 * | 10/2020 | Pancholy | A61B 17/1325 |
| 2021/0219987 | A1 * | 7/2021 | Pancholy | A61B 17/12 |
| 2022/0257253 | A1 * | 8/2022 | Pancholy | A61B 17/12 |
| 2024/0065705 | A1 * | 2/2024 | Pancholy | A61B 17/1325 |
| 2024/0065706 | A1 * | 2/2024 | Pancholy | A61B 5/0295 |
| 2025/0072898 | A1 * | 3/2025 | Pancholy | A61B 17/135 |

* cited by examiner

METHOD TO STOP BLEEDING, WITH SHORT HEMOSTASIS DURATION USING A LOW DOSE OF ANTICOAGULANT

CROSS-REFERENCE TO RELATED APPLICATIONS

This application is a continuation of U.S. patent application Ser. No. 17/736,213, filed May 4, 2022, which is a continuation of U.S. patent application Ser. No. 16/829,317, filed Mar. 25, 2020, now U.S. Pat. No. 11,350,943 issued on Jun. 7, 2022, which is a continuation of U.S. patent application Ser. No. 15/924,273, filed Mar. 18, 2018, now U.S. Pat. No. 10,639,042 issued May 5, 2020, which is a continuation of U.S. patent application Ser. No. 15/426,056, filed Feb. 7, 2017, now U.S. Pat. No. 9,949,738 issued Apr. 24, 2018, which is a continuation-in-part of U.S. patent application Ser. No. 15/340,023, filed Nov. 1, 2016, now U.S. Pat. No. 9,592,060 issued Mar. 14, 2017, which is a continuation of U.S. patent application Ser. No. 15/062,150, filed Mar. 6, 2016, now U.S. Pat. No. 9,510,838 issued Dec. 6, 2016, which is a continuation of U.S. patent application Ser. No. 13/941,219, filed Jul. 12, 2013, now U.S. Pat. No. 9,308,000 issued Apr. 12, 2016.

BACKGROUND OF INVENTION a. Field of Invention

The invention relates generally to transradial catheterization methods and devices used in said methods. In particular, the invention concerns a method of obtaining patent hemostasis of the radial artery by compressing the un-instrumented ulnar artery to increase radial artery flow while applying pressure to the radial artery access site. The invention further concerns a device for applying blunt pressure to the ulnar artery, and a method of use.

b. Description of Related Art

Radial artery instrumentation is becoming increasingly prevalent with cardiovascular procedures performed via transradial access, providing improvement in outcomes, cost, as well as comfort. Radial artery occlusion refers to the blockage of the radial artery. Radial artery occlusion is a consequence of radial artery cannulation, which obliterates the radial artery lumen, making it not available for access in the future.

After instrumentation, it is necessary to compress the radial artery at the access site to obtain hemostasis of the cannulation wound. The cannulation wound is an opening of the wall of the radial artery. Hemostasis of the cannulation (or sheath) wound is accomplished by applying blunt pressure to the radial artery at the cannulation wound site, or access site. The application of this blunt pressure on the radial artery often causes the artery to occlude or close, thereby denying bloodflow further downstream within the radial artery. Maintaining blood flow in the radial artery while compressing the access site, after instrumentation, reduces the risk of post-instrumentation radial artery occlusion. Patent hemostasis is therefore understood to mean achieving the cessation of bleeding at the cannulation wound (access site) of the radial artery, while blood is allowed to flow through the artery.

The following references are representative of the field pertaining to the present invention:

For example, U.S. Pat. No. 6,355,026 to Mick describes right and left coronary catheters that are designed to be used in a transradial coronary catheterization. Also discussed are methods of inserting the catheters into a right or left coronary artery by a transradial approach.

In an article entitled Efficacy and Safety of Transient Ulnar Artery Compression to Recanalize Acute Radial Artery Occlusion After Transradial Catheterization (Am J Cardiol 2011; 107:1698-1701) Ivo Bernat, MD, and others, discuss a method directed to open an occluded radial artery after the radial artery becomes occluded. In the case of radial artery occlusion, 3-4 hours after hemostasis of the radial artery, ulnar artery compression was applied to attempt recanalization of radial artery. Bernat et. al. verified reopening of the radial artery by administration of heparin and compression of the ulnar artery.

Transradial access is being increasingly used because of its ability to reduce access-site complications and increase patient comfort. While performing transradial catheterization, upon introduction of the introducer sheath or catheter into the radial artery, it is best practice to administer anticoagulant, e.g., unfractionated heparin, bivalirudin or Enoxaparin, to assist in the prevention of radial artery occlusion, even when the catheterization procedure itself would otherwise not require it. Anticoagulants may also be referred to as blood thinners. The prophylactic effect of an anticoagulant such as unfractionated heparin to reduce the occurrence of radial artery occlusion is dose-dependent with significantly better efficacy with higher doses. With the administration of 5000 units of unfractionated heparin or alternatively 50 units per kilogram (kg) of body weight, radial artery occlusion rates have been reported in the range of 4-5%. Doses of heparin to be administered are generally expressed in units of heparin per kg of body weight. A conventional dose of unfractionated heparin during a transradial catheterization procedure is about 50 units per kg of body weight. A conventional dose of other anticoagulants, such as Bivalirudin or Enoxaparin is the equivalent of 50 units of unfractionated heparin per kg of body weight.

In view of the anticoagulant effect of unfractionated heparin, which effect typically exceeds the duration of the cardiovascular procedure, the patient is systemically anticoagulated with observed activated clotting times of approximately 200-225 seconds, while undergoing hemostasis. Optimally, a minimum duration of about 120 minutes of compression at the radial artery access site is required to achieve hemostasis.

SUMMARY OF INVENTION

A present invention method of catheterization of the radial artery directed at minimizing occurrences of radial artery occlusion is disclosed. The method comprises inserting a sheath into the radial artery of a patient at an access site. The desired catheterization procedure is then performed using the sheath to access the radial artery. Once the catheterization procedure is complete, an ulnar pressure is applied to the homolateral ulnar artery at an ulnar pressure site while the sheath remains inserted in the radial artery. The sheath is then removed from the radial artery while maintaining the ulnar pressure to the ulnar artery. Once the sheath is removed, and while continuing to apply the ulnar pressure, pressure is applied to the radial artery at the access site to obtain hemostasis at the access site.

In a preferred embodiment, the step of "applying a pressure to the radial artery at the access site to obtain hemostasis at the access site" is accomplished while maintaining the ulnar pressure to the ulnar artery.

In an embodiment of the present invention, a further step includes confirming that the step of applying ulnar pressure has reduced blood flow through the ulnar artery by monitoring flow of the ulnar artery prior to and after applying the ulnar pressure. In a further embodiment, monitoring flow of the ulnar artery includes sensing skin blood flow and/or pulsation at a fingertip or other location downstream of the ulnar pressure site. Digital plethysmography is employed in a preferred embodiment.

In another embodiment, the method further includes confirming patency of the radial artery during the step of applying a pressure to the radial artery by sensing skin blood flow and/or pulsation at a fingertip or other location downstream of the access site. In this embodiment, the sensing is performed while the ulnar artery is fully compressed (allowing no flow through the ulnar artery) and/or partially compressed (allowing less flow than when not compressed at all). Patency is confirmed, in an embodiment, by obtaining a metric relating to the sensing and comparing the metric with a standard metric for the patient, or with a previously-sensed metric. Preferably, the previously sensed metric is read after the applying the ulnar pressure step and before the step of removing the sheath from the radial artery. Digital plethysmography is employed in a preferred embodiment. In yet another embodiment, the method further includes administering anticoagulant at a dose lower than the conventional dose when an increased flow of blood is provided in the artery that is punctured at the access site.

In an embodiment of the present invention method, the step of compressing the ulnar artery includes: providing an ulnar impinger, securing the ulnar impinger over the wrist such that the impinger contacts a first location over the ulnar artery, and activating the impinger to press on the ulnar artery at the first location.

In a preferred embodiment of the present invention, the step of compressing the ulnar artery includes: providing an ulnar impingement band having an inflatable bladder, securing the ulnar impingement band over the wrist such that the bladder contacts a first location over the ulnar artery, and inflating the bladder to impinge upon the ulnar artery at the first location.

There is further disclosed a device for use in applying a compressing force to the ulnar artery of a patient. The device includes a trunk having an inflatable bladder. The trunk is defined by a lower portion and an upper portion. The bladder is defined by an expandable envelopment existing between the lower portion and the upper portion. A pair of limbs are connected to and extend from the upper portion of the trunk. Together, the pair of limbs and the trunk form a general Y-shape. A first limb of the pair of limbs is adapted to lay across the palm of a hand, between the thumb and the index finger and connect to the trunk to secure the first limb to the trunk and to secure the bladder to a portion of the patient's wrist corresponding with a first location over the ulnar artery. A second limb of the pair of limbs is adapted to lay over the wrist/distal forearm and connect to the trunk. This is to secure the second limb to the trunk and to further secure the bladder to the first location over the ulnar artery. One or more connectors are utilized for fixing the pair of limbs to the trunk.

In use, the bladder is located at the first location over the ulnar artery, and the pair of limbs are fixed around the hand and wrist to the trunk with the connectors. The bladder is inflated with a tube connected to an inflator to cause the bladder to impinge upon the ulnar artery at the first location.

There is further disclosed a device for use in applying a compressing force to the ulnar artery of a patient. The device comprises a trunk having an impinger. The trunk is defined by a lower portion and an upper portion. The impinger is defined by any device sufficient to apply a compression force. A pair of limbs are connected to and extend from the upper portion of the trunk. The pair of limbs together with the trunk form a general Y-shape. A first limb of the pair of limbs is adapted to lay across the palm of a hand, between the thumb and the index finger. The first limb connects to the trunk to secure the first limb to the trunk, and also to secure the impinger to a portion of the patient's wrist corresponding with a first location over the ulnar artery. A second limb of the pair of limbs is adapted to lay over the wrist/distal forearm and connect to the trunk to secure the second limb to the trunk and to further secure the bladder to the first location over the ulnar artery. One or more connectors are employed to fix the pair of limbs to the trunk. In use, the impinger is located at the first location over the ulnar artery. The pair of limbs are fixed around the hand and wrist to the trunk with the connectors. The impinger is activated to cause the bladder to impinge upon the ulnar artery at the first location.

Additional features, advantages, and embodiments of the invention may be set forth or are apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings.

DETAILED DESCRIPTION OF THE EMBODIMENTS

The invention is directed to a method of obtaining patent hemostasis of the radial artery by compressing the uninstrumented ulnar artery to increase radial artery flow while applying pressure to the radial artery access site. The invention further concerns a device for applying blunt pressure to the ulnar artery, and a method of use.

Figure 1:
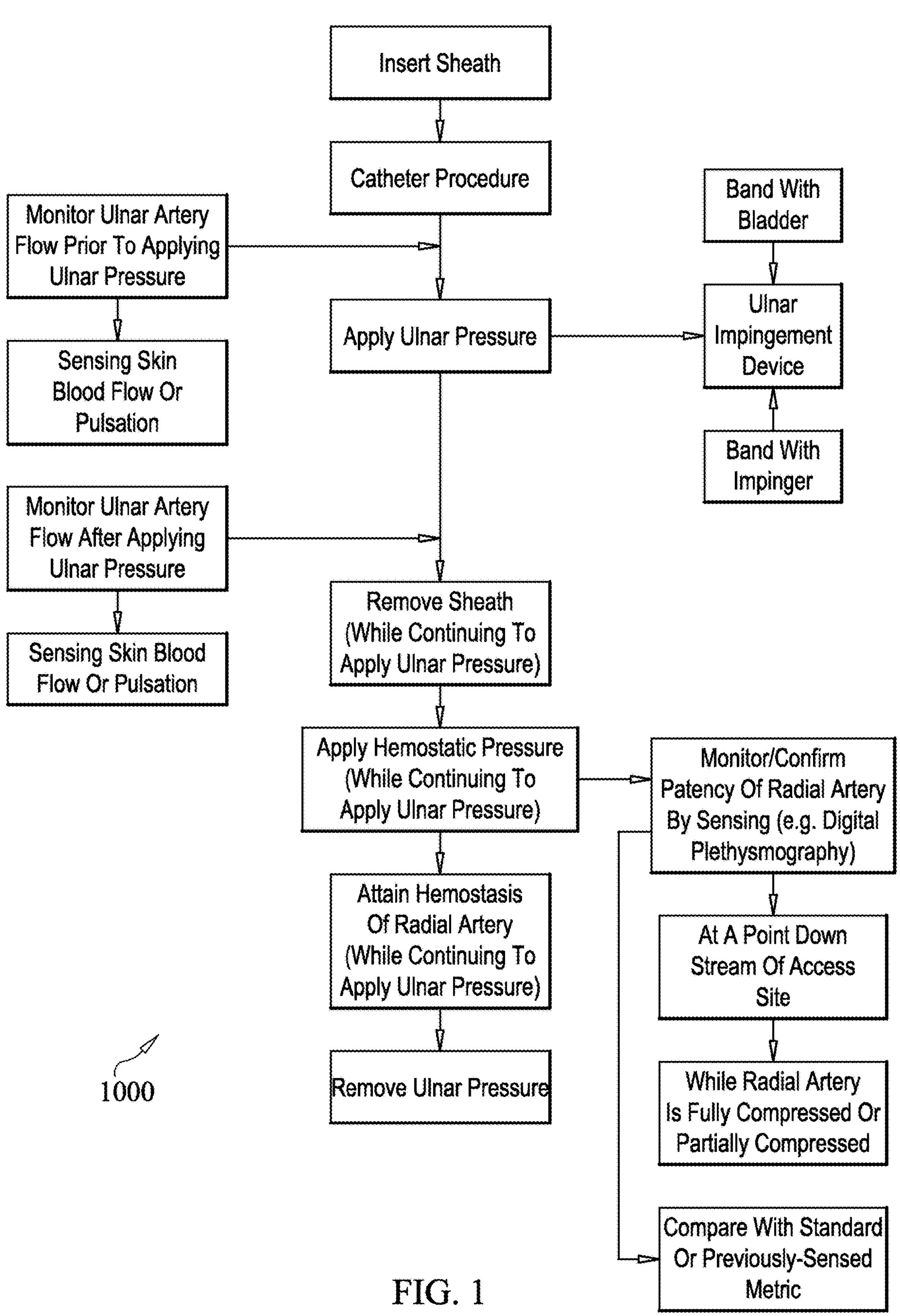
FIG. 1 is schematic layout of methods disclosed herein.
Figure 2:
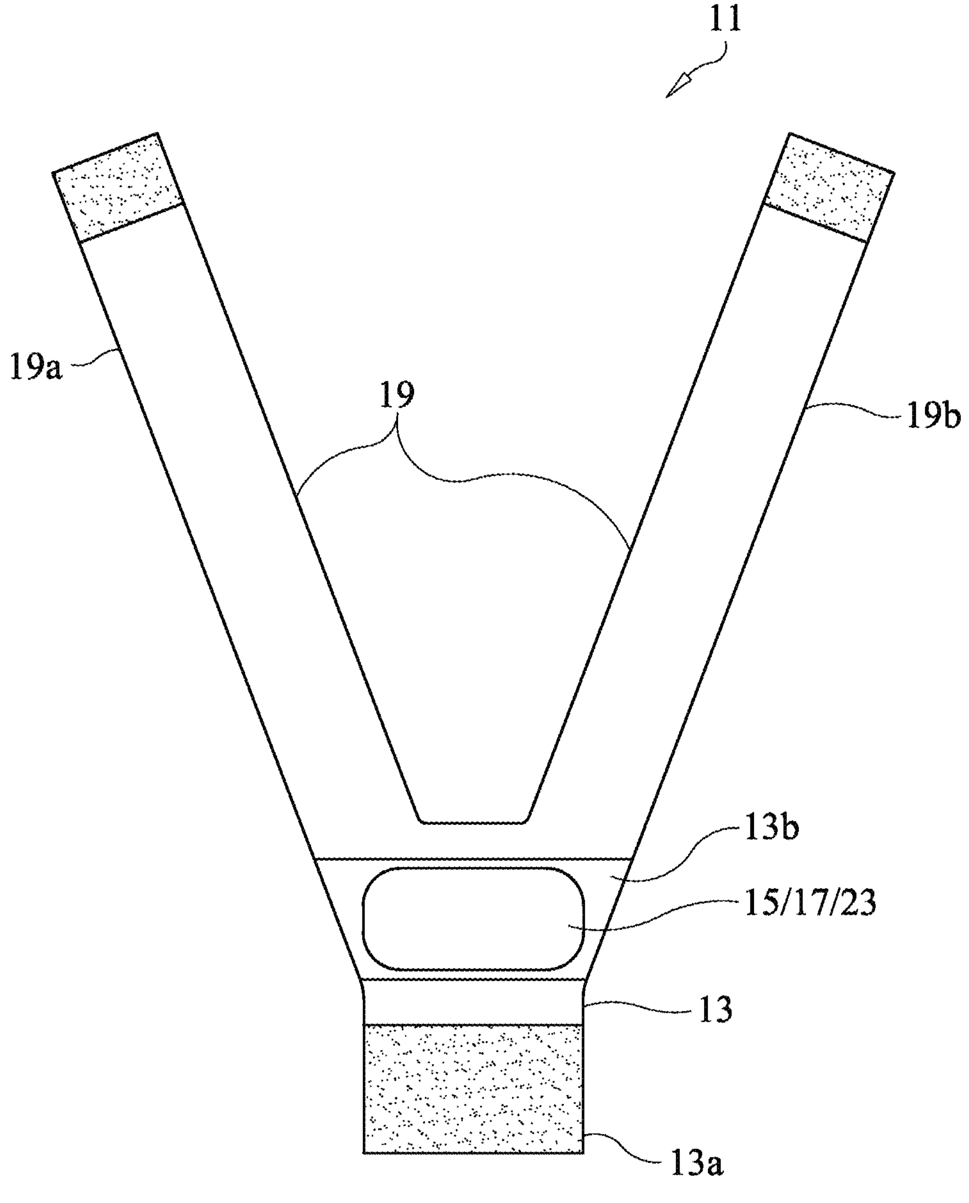
FIG. 2 is a plan view of the ulnar impingement device according to an embodiment of the present invention.
Figure 3:
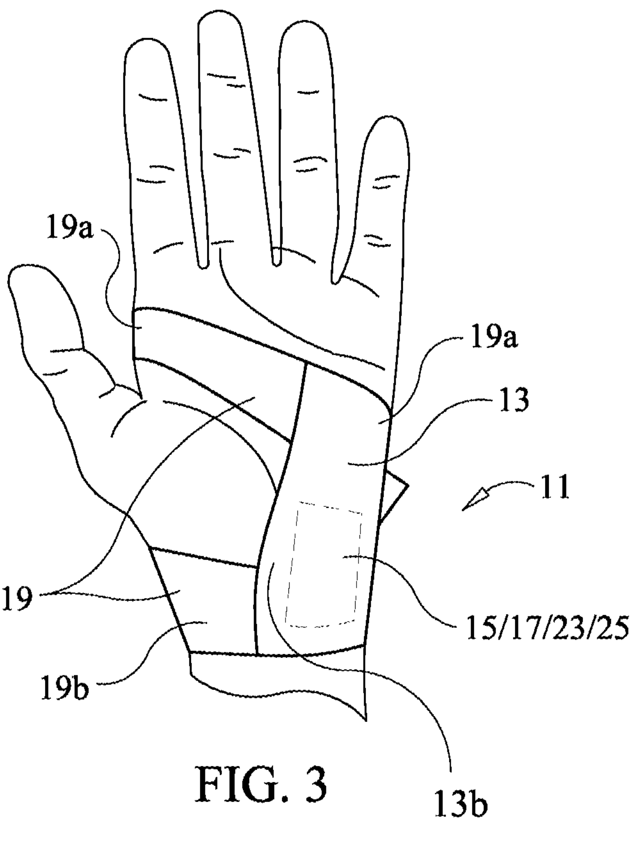
FIG. 3 is a view showing the ulnar impingement device applied to a patient according to an embodiment of the present invention.
Figure 4:
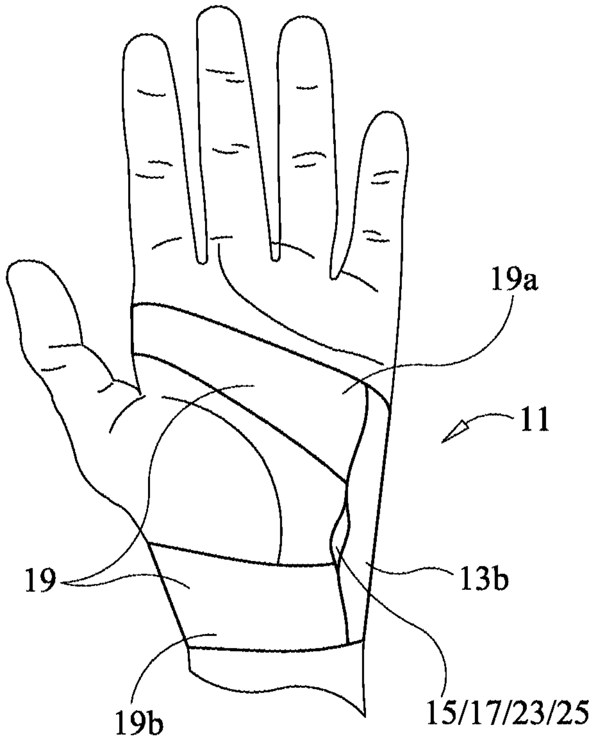
FIG. 4 is another view showing the bladder or impinger of the ulnar impingement device applied to a patient according to an embodiment of the present invention.
Figure 5:
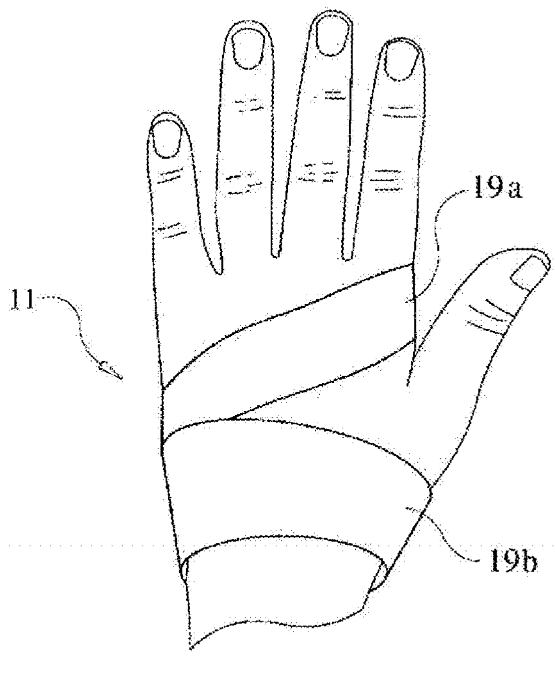
FIG. 5 is a view showing the ulnar impingement device applied to a patient showing the top of the hand according to an embodiment of the present invention.
Figure 6:
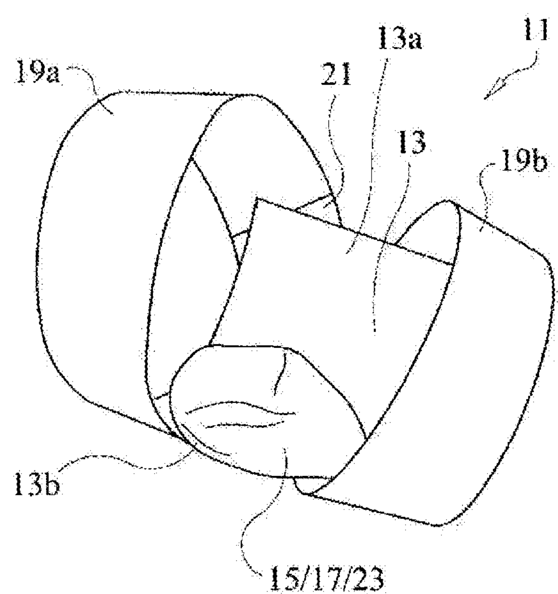
FIG. 6 is an isometric view of the ulnar impingement device shown with trunk fastened to the pair of limbs.

A present invention method of catheterization of the radial artery directed at minimizing occurrences of radial artery occlusion is disclosed. Referring to FIG. 1 specifically, and the Figures in general, the method 1000 comprises inserting a sheath into the radial artery of a patient at an access site. A sheath, as disclosed herein, is understood to encompass any device inserted into the radial artery and used to permit the access of instrumentation into the radial artery. The desired catheterization procedure is then performed using the sheath to provide instrumentation access the radial artery.

Once the catheterization procedure is complete, an ulnar pressure is applied to the homolateral ulnar artery at an ulnar pressure site while the sheath remains inserted in the radial artery. The sheath is then removed from the radial artery while maintaining the first pressure to the ulnar artery. Once the sheath is removed, and while continuing to apply the ulnar pressure, pressure is applied to the radial artery at the access site to obtain hemostasis at the access site.

In a preferred embodiment, the step of "applying a pressure to the radial artery at the access site to obtain hemostasis at the access site" is accomplished while maintaining the first pressure to the ulnar artery.

The radial artery and the ulnar artery are the two conduits for the flow of oxygenated blood to the hand. The arteries are interconnected and therefore form an interdependent flow network. When flow is reduced in one of the arteries, by compression for example, flow increases in the other artery. When the ulnar artery is compressed, flow in the ulnar artery is reduced, which causes an increase in pressure and flow in the radial artery. When the radial artery is compressed, flow in the radial artery is reduced, which causes an increase in pressure and flow in the ulnar artery.

In an embodiment, a further step includes confirming that the application of ulnar pressure has reduced blood flow through the ulnar artery. This is done by monitoring flow of the ulnar artery prior to and after applying the ulnar pressure. In a further embodiment, monitoring flow of the ulnar artery includes sensing skin blood flow and/or pulsation at a fingertip or other location downstream of the ulnar pressure site. Digital plethysmography is employed in one embodiment.

In another embodiment, the method 1000 further includes confirming patency of the radial artery during the step of applying a pressure to the radial artery. In a preferred embodiment, patency is accomplished by sensing skin blood flow and/or pulsation at a fingertip or other location downstream of the access site. Other sensing locations both upstream and downstream may be used to confirm patency of the radial artery. In the preferred embodiment, the sensing is performed while the ulnar artery is fully compressed (allowing no flow through the ulnar artery) and/or partially compressed (allowing less flow than when not compressed at all). Patency is confirmed, in an embodiment, by obtaining a metric relating to the sensing and comparing the metric with a standard metric for the patient, or with a previously-sensed metric. Metric is understood to mean a sensible, quantifiable value or reading, relating to the characteristic sensed. Preferably, the previously sensed metric is read after the applying the ulnar pressure step and before the step of removing the sheath from the radial artery. Digital plethysmography is employed, in a preferred embodiment, to obtain the metrics. Other sensing modes may be employed, so long as the selected mode is capable of confirming patency in one form or another.

In an embodiment of the present invention method 1000, the step of compressing the ulnar artery includes: providing an ulnar impinger, securing the ulnar impinger over the wrist such that the impinger contacts a first location over the ulnar artery, and activating the impinger to press on the ulnar artery at the first location. In a preferred embodiment, the first location is over the Guyon's canal, demarcated by pisiform bone on the medial aspect, directly over the ulnar artery pulse.

Impinger is understood to include any device capable of applying a force to the ulnar artery, whether alone or part of a system, sufficient to compress the ulnar artery. One exemplary class includes mechanical devices that expand in size to cause a band surrounding the wrist to constrict an object to compress the ulnar artery. Another exemplary class of impingers includes mechanical devices that constrict a band worn around the wrist sufficient to cause an object to press on the ulnar artery.

In a preferred embodiment, the step of compressing the ulnar artery includes: providing an ulnar impingement band having an inflatable bladder, securing the ulnar impingement band over the wrist such that the bladder contacts a first location over the ulnar artery, and inflating the bladder to impinge upon the ulnar artery at the first location.

Turning to the Figures generally, and particularly FIGS. 2-6, there is further disclosed a device 11 for use in applying a compressing force to the ulnar artery of a patient. The device 11 includes a trunk 13 having an inflatable bladder 15. The trunk 13 is defined by a lower portion 13*a* and an upper portion 13*b*. The bladder 15 is defined by an envelopment 17 existing between the lower portion 13*a* and the upper portion 13*b*. A pair of limbs 19 are connected to and extend from the upper portion 13*b* of the trunk 13. Together, the pair of limbs 19 and the trunk 13 form a general Y-shape. Preferably, the pair of limbs 19 and the trunk 13 are planar and form a Y-shape band. A first limb 19*a* of the pair of limbs 19 is adapted to lay across the palm of a hand, between the thumb and the index finger. The first limb 19*a* is adapted to connect to the trunk 13 for securing the first limb 19*a* to the trunk 13 and for securing the bladder 15 to a portion of the patient's wrist corresponding with a first location 25 over the ulnar artery. A second limb 19*b* of the pair of limbs 19 is adapted to lay over the wrist/distal forearm and connect to the trunk 13. This is to secure the second limb 19*b* to the trunk 13 and to further secure the bladder 15 to the first location 25 over the ulnar artery. One or more connectors 21 are utilized for fixing the pair of limbs 19 to the trunk 13. In a preferred embodiment, the connector is Velcro.

In use, the bladder 15 is located at the first location 25 over the ulnar artery, and the pair of limbs 19 are fixed around the hand and wrist to the trunk 13 with the connectors 21. The bladder 15 is inflated with a tube connected to an inflator to cause the bladder 15 to impinge upon the ulnar artery at the first location 25.

There is further disclosed a device 13 for use in applying a compressing force to the ulnar artery of a patient. The device 13 comprises a trunk 13 having an impinger 23. The trunk 13 is defined by a lower portion 13*a* and an upper portion 13*b*. The impinger 23 is defined by any device sufficient to apply a compression force. Examples include expanding springs, expanding screw-type appurtenances, or other devices and systems as discussed herein. A pair of limbs 19 are connected to and extend from the upper portion 13*b* of the trunk 13. The pair of limbs 19 together with the trunk 13 form a general Y-shape. A first limb 19*a* of the pair of limbs 19 is adapted to lay across the palm of a hand, between the thumb and the index finger. The first limb 19*a* connects to the trunk 13 to secure the first limb 19*a* to the trunk 13, and also to secure the impinger 23 to a portion of the patient's wrist corresponding with a first location 25 over the ulnar artery. A second limb 19*b* of the pair of limbs 19 is adapted to lay over the wrist/distal forearm and connect to the trunk 13 to secure the second limb 19*b* to the trunk 13 and to further secure the impinge 23 to the first location over the ulnar artery. One or more connectors 21 are employed to fix the pair of limbs 19 to the trunk 13. In use, the impinger 23 is located at the first location 25 over the ulnar artery. The pair of limbs 19 are fixed around the hand and wrist to the trunk 13 with the connectors 21. The impinger 23 is activated to cause the impinger 23 to impinge upon the ulnar artery at the first location 25.

In another embodiment of the present invention method 1000, an introducer sheath and/or a catheter is placed in a radial artery after sterile preparation as well as with administration of local anesthetic. The radial artery is punctured at an access site and, after placement of a guidewire, either an introducer sheath or a catheter is introduced in the radial artery lumen. The catheterization procedure is performed in a manner deemed appropriate by the operator.

In one embodiment, the present invention method further comprises administering an anticoagulant at any time after introduction of the catheter or introducer sheath and before removal of the catheter or the introducer sheath. In another embodiment, an anticoagulant is administered before the introduction of the catheter or introducer sheath. Examples of anticoagulants include, without limitation, unfractionated heparin, bivalirudin or Enoxaparin. In one embodiment wherein a method for obtaining patent hemostasis at an access site of an artery comprises increasing the flow of blood in the artery that is punctured at the access site, unfractionated heparin is administered at a dose that is lower than the conventional dose. The flow of blood may be increased in the radial artery if the radial artery is punctured for catheterization, the ulnar artery if the ulnar artery is punctured for catheterization, or any other artery that is punctured at an access site.

Another coagulant may also be used at a dose that is lower than the conventional dose. An anticoagulant may be selected from a group comprising heparin, dalteparin, Fragmin®, danaparoid, enoxaparin, unfractionated heparin, other low molecular weight heparin, direct thrombin inhibitors including hirudin, argatroban, bivalirudin and all substances derived from and/or related to the foregoing substances.

In one embodiment, the anticoagulant is unfractionated heparin and the dosage of the unfractionated heparin is less than 50 units per kilogram of body weight, administered parenterally. In yet another embodiment, the dosage of unfractionated heparin is about 25 units per kilogram of body weight. In another embodiment, the dosage of unfractionated heparin is less than 25 units per kilogram of body weight. In yet another embodiment, the dosage of unfractionated heparin is in the range of 20-40 units per kilogram of body weight. In another embodiments, the dosage of unfractionated heparin is in the range of 15-30 units per kilogram of body weight.

After completion of the catheterization procedure, the present invention method comprises applying hemostatic compression to the access site using a device. In one embodiment, the device is a band having at least two inflatable bladders wherein one inflatable bladder is used to apply compressive hemostatic pressure at the access site on the radial artery, and a second inflatable bladder is used to apply an ulnar pressure at an ulnar pressure site. In another embodiment, a device such as an impinger that is capable of applying a mechanical compressive force is used to apply the ulnar pressure. In yet another embodiment, a band with at least one inflatable bladder is used to apply compressive hemostatic pressure at the access site on the radial artery, and another device is used to apply ulnar pressure at an ulnar pressure site. Manual compression may also be used.

In one embodiment of the present invention method, wherein an anticoagulant such as unfractionated heparin is administered to a patient, the method further comprises applying hemostatic compression for a time less than 120 minutes. In another embodiment, the hemostatic compression time is about 60 minutes. In yet another embodiment, the hemostatic compression time is less than 60 minutes. In one embodiment, during the hemostatic compression time when the radial artery is compressed at the access site, the ipsilateral ulnar artery is also compressed simultaneously. In another embodiment, the ipsilateral ulnar artery is compressed continuously during the entire hemostatic compression time. In yet another embodiment, the ipsilateral ulnar artery is compressed continuously for only a part of the hemostatic compression time. In another embodiment, the ulnar artery is compressed intermittently during the hemostatic compression time. In some embodiments, the ulnar artery may be compressed fully, and in other embodiments, the ulnar artery may be compressed partially.

In one embodiment of present invention, a method of obtaining hemostasis of a radial artery of a patient after performing a catheterization procedure at an access site of the radial artery, comprises performing the following steps: (a) applying a hemostatic pressure to the radial artery at the access site; (b) providing an increased flow of blood in the radial artery; (c) administering a dose of unfractionated heparin to the patient; and (d) maintaining simultaneously the hemostatic pressure and the increased flow of blood in the radial artery; wherein step (b) comprises applying an ulnar pressure to an ulnar artery at an ulnar pressure site; and wherein step (c) comprises administering the dose of unfractionated heparin that is less than 50 units per kg body weight.

In another embodiment of present invention, a method of obtaining hemostasis of an artery of a patient after performing a catheterization procedure at an access site of the artery, comprises performing the following steps: (i) applying a hemostatic pressure to the artery at the access site; (ii) providing an increased flow of blood in the artery; (iii) administering a dose of unfractionated heparin to the patient; and (iv) maintaining simultaneously the hemostatic pressure and the increased flow of blood in the artery for a duration of time; wherein step (iii) comprises administering the dose of unfractionated heparin that is less than 50 units per kg body weight; and wherein the duration of time in step (iv) is less than 120 minutes.

In yet another embodiment of present invention, a method of obtaining hemostasis of a radial artery of a patient after performing a catheterization procedure at an access site of the radial artery, comprising performing the following steps: (A) applying a hemostatic pressure to the radial artery at the access site; (B) providing an increased flow of blood in the radial artery; (C) administering a dose of an anticoagulant to the patient; and (D) maintaining simultaneously the hemostatic pressure and the increased flow of blood in the radial artery for a duration of time; wherein step (B) comprises applying an ulnar pressure to an ulnar artery at an ulnar pressure site; wherein the dose of the anticoagulant in step (C) is less than an equivalent of 50 units of unfractionated heparin per kg of body weight; and wherein the duration of time in step (D) is less than 120 minutes.

In one embodiment of the present invention, a hemostatic pressure on the radial artery is applied using a first band comprising at least one inflatable bladder, wherein the inflatable bladder of the first band applies the hemostatic pressure at the access site, and the ulnar pressure is applied using a technique selected from a group consisting of (i) a second band comprising at least one inflatable bladder, wherein the inflatable bladder of the second band applies a pressure at the ulnar pressure site, (ii) a mechanical device applies a compressing force at the ulnar pressure site; (iii) manual pressure is applied at the ulnar pressure site.

In one embodiment, after about 60 minutes of compression of the radial artery at the access site, the pressure of compression is gradually reduced and weaned off from the radial artery access site, and the site is lightly dressed. The duration of reducing the compression and weaning off the hemostatic compression pressure is in the range of 5-10 minutes. This technique improves patient comfort and increases the number of patients who can be treated.

The invention claimed is:

1. A method of obtaining patent hemostasis of a radial artery of a patient when performing a catheterization procedure at an access site of the radial artery, comprising performing the following steps:

(a) administering a dose of anticoagulant to the patient during the catheterization procedure, wherein the dose of anticoagulant is less than an equivalent of 50 units of unfractionated heparin per kg of body weight;

(b) applying a compressive pressure to the radial artery at the access site for a duration of time, wherein the duration of time is less than 120 minutes;

(c) attaining patent hemostasis of the radial artery;

wherein step (a) comprises administering anticoagulant at any time after introduction of a catheter or an introducer sheath and before removal of the catheter or the introducer sheath; and wherein step (b) comprises the compressive pressure to the radial artery being applied using a first band comprising at least a first inflatable bladder, the first inflatable bladder applying a compressive pressure to the radial artery at the access site.

2. The method of claim 1, further comprising a step of monitoring and/or confirming patency of the radial artery, the step of monitoring and/or confirming patency of the radial artery being performed by sensing skin blood flow and/or pulsation at a fingertip or other location downstream of the access site.

3. The method of claim 2, wherein the step of confirming patency includes the use of digital plethysmography.

4. The method of claim 1, where the anticoagulant is selected from a group consisting of: heparin, dalteparin, danaparoid, enoxaparin, unfractionated heparin, low molecular weight heparin, direct thrombin inhibitors including hirudin, argatroban, bivalirudin, and combinations or derivatives thereof.

5. The method of claim 1, wherein the dose of anticoagulant in step (a) is about an equivalent of 25 units of unfractionated heparin per kg of body weight.

6. The method of claim 1, wherein the dose of anticoagulant in step (a) is less than an equivalent of 25 units of unfractionated heparin per kg of body weight.

7. The method of claim 1, wherein the dose of anticoagulant in step (a) is in the range of an equivalent of 20-40 units of unfractionated heparin per kg of body weight.

8. The method of claim 1, wherein the dose of anticoagulant in step (a) is in the range of an equivalent of 15-30 units of unfractionated heparin per kg of body weight.

9. The method of claim 1, wherein the duration of time is about 60 minutes.

10. The method of claim 1, wherein the duration of time is less than 60 minutes.

11. The method of claim 1, wherein the compressive pressure to the radial artery in step (b) is gradually reduced after about 60 minutes of compression of the radial artery at the access site.

12. The method of claim 1, wherein the compressive pressure to the radial artery in step (b) is gradually reduced and weaned off from the radial artery access site, and the site is lightly dressed.

13. The method of claim 12, wherein the duration of weaning off the compressive pressure to the radial artery is in the range of 5-10 minutes.

14. The method of claim 1, further comprising applying a compressive pressure to an ipsilateral ulnar artery at an ulnar pressure site.

15. The method of claim 14, further comprising applying the compressive pressure to the ipsilateral ulnar artery using at least a second inflatable bladder, the first band comprising the second inflatable bladder.

16. The method of claim 14, wherein the compressive pressure to the ipsilateral ulnar artery is applied using a technique selected from a group consisting of (i) a second band comprising at least a second inflatable bladder, wherein the second bladder applies the ulnar pressure, (ii) a mechanical device applies a compressing force at the ulnar pressure site; (iii) manual pressure is applied at the ulnar pressure site.

17. The method of claim 14, wherein applying the compressive pressure to the ipsilateral ulnar artery compresses the ulnar artery partially or fully.

18. The method of claim 14, wherein the compressive pressure to the ipsilateral ulnar artery is applied intermittently.

19. The method of claim 14, wherein the compressive pressure to the ipsilateral ulnar artery is applied continuously.

20. A method of obtaining patent hemostasis of a radial artery of a patient when performing a catheterization procedure at an access site of the radial artery, comprising performing the following steps:

(a) administering a dose of anticoagulant to the patient during the catheterization procedure, wherein the dose of anticoagulant is less than an equivalent of 50 units of unfractionated heparin per kg of body weight;

(b) applying a compressive pressure to the radial artery at the access site for a duration of time, wherein the duration of time is less than 120 minutes;

(c) monitoring and/or confirming patency of the radial artery, the step of monitoring and/or confirming patency of the radial artery being performed by sensing skin blood flow and/or pulsation at a fingertip or other location downstream of the access site;

(d) attaining patent hemostasis of the radial artery;

wherein step (a) comprises administering anticoagulant at any time after introduction of a catheter or an introducer sheath and before removal of the catheter or the introducer sheath; wherein step (b) comprises the compressive pressure to the radial artery being applied using a first band comprising at least a first inflatable bladder, the first inflatable bladder applying a compressive pressure to the radial artery at the access site; and wherein the compressive pressure to the radial artery in step (b) is gradually reduced and weaned off from the radial artery access site.

* * * * *